US005484587A

United States Patent [19]
Branly et al.

[11] Patent Number: 5,484,587
[45] Date of Patent: Jan. 16, 1996

[54] DIABROTICINE BAIT

[75] Inventors: Keith Branly, Brandon, Fla.; James M. Gaggero, Citrus Heights, Calif.; Chel W. Lew; Cathy S. Lamb, both of San Antonio, Tex.

[73] Assignee: Micro Flo Company, Mulberry, Fla.

[21] Appl. No.: 784,506

[22] Filed: Oct. 31, 1991

[51] Int. Cl.⁶ .......................... A01N 25/28; A01N 65/00; A01N 47/10

[52] U.S. Cl. .......................... 424/84; 424/405; 424/406; 424/410; 424/499; 424/500; 424/DIG. 8; 424/195.1; 514/478; 514/510

[58] Field of Search .......................... 424/405, 408, 424/84, 406, 410

[56] References Cited

U.S. PATENT DOCUMENTS

| | | | |
|---|---|---|---|
| 4,615,883 | 10/1986 | Nelsen et al. | 424/84 |
| 4,764,372 | 8/1988 | Hermstadt et al. | 424/93 |
| 4,985,413 | 1/1991 | Kohama et al. | 514/79 |
| 5,120,540 | 6/1992 | Doane et al. | 424/195.1 |

FOREIGN PATENT DOCUMENTS

| | | | |
|---|---|---|---|
| 1195922 | 6/1983 | Canada | 424/84 |
| 85/04074 | 3/1984 | WIPO . | |

OTHER PUBLICATIONS

Corn Insects Project, "Field Cage and Laboratory Evaluation of Semiochemical-based Baits", *Report to NCR-46 Corn Rootworm Technical Committee*, Minneapolis, Minn. Jan. 24 & 25, 1989.

Weissling et al., "Summary of 1988 Experiments with Starch Encapsulated Semiochemicals and Insecticides", *Report to NCR-46 Corn Rootworm Technical Committee, Minneapolis, Minn. Jan. 24 & 25, 1989.*

Corn Insects Project, "Limited Field Trials of Semiochemical-based Bait for Control of Adult Northern and Western Corn Rootworms", presentation to NCR-46 Corn Rootworm Technical Committee, Indianapolis, In., Jan. 16-17, 1990.

Corn Insects Project, "Effects of Particle Size, Distribution, and Attractant Content on Efficacy of Semiochemical-based Baits in Walk-in Field Cages", presentation to NCR-46 Corn Rootworm Technical Committee, Grand Rapids, Mich., Jan. 16-17, 1990.

Weissling et al., "Effect of Starch-based Corn Rootworm Baits on Selected Nontarget Insect Species: Influence of Semiochemical Composition", *J. Econ. Entomol.*, 84(4), 1235-1241 (Aug. 1991).

Weissling et al., "Effect of Starch-based Corn Rootworm Baits on Selected Nontarget Insect Species: Influence of Semiochemical Composition", abstract presented at the Entomological Society of America North Central Branch Meeting, Mar. 1990.

Levine et al., "Control of Western Corn Rootworms with Semiochemical Baits in Illinois", abstract presented at Entomological Society of America North Central Branch Meeting, Mar. 1990.

I. Aguinagalde, J. M. Ortiz, F. Rodriguez and C. Cedano, "Chemosystematic Survey of Cultivated *Cucurbita* Species," Journal of Horticultural Science, 65(6):649-655, (1990).

J. F. Andersen and R. L. Metcalf, "Identification To A Volatile Attractant For *Diabrotica* and *Acalymma* SPP. From Blossoms of *Cucurbita maxima* Duchesne", Journal of Chemical Ecology, vol. 12, No. 3, pp. 687-699 (1986).

J. F. Andersen and R. L. Metcalf, "Factors Influencing Distribution of *Diabrotica* SPP. In Blossoms of Cultivated *Cucurbita* SPP.," Journal of Chemical Ecology, vol. 13, No. 4, pp. 681-699 (1987).

(List continued on next page.)

Primary Examiner—Thurman K. Page
Assistant Examiner—Neil Levy
Attorney, Agent, or Firm—Banner, Birch, McKie & Beckett

[57] ABSTRACT

Baits for diabroticine beetles are microspherical particles containing a homogeneous mixture of a toxicant for diabroticine beetles and a feeding stimulant in a binder containing a gelatin and a gum. Preferred formulations include carbaryl and buffalo gourd root powder.

31 Claims, 3 Drawing Sheets

OTHER PUBLICATIONS

M. Arisawa, J. M. Pezzuto, A. D. Kinghorn, G. A. Cordell and N. R. Farnsworth, "Plant Anticancer Agents XXX: Cucurbitacins from *Ipomopsis Aggregata* (Polemoniaceae)," Journal of Pharmaceutical Sciences, vol. 73, No. 3, pp. 411–413 (1984).

Tom Arthur, "New Approach To Rootworm Control: Manipulating adult populations may one day greatly enhance corn rootworm control", Farm Chemicals, (Jul. 1989).

Mohamed A. Ba–Amer and W. P. Bemis, "Fruit and Seed Development in *Cucurbita foetidissima*," pp. 297–299(1968).

J. W. Berry, A. C. Gathman, J. M. Nelson, J. C. Scheerens, "Buffalo Group Research Status and Potential for Commercialization as a Cucurbitacin Source", (Apr. 1985).

J. W. Berry, J. C. Scheerens and W. P. Bemis, "Buffalo Gourd Roots: Chemical Composition and Seasonal Changes in Starch Content", J. Agric. Food Chem., vol. 26, No. 2, pp. 354–356 (1978); Cucurbit Root Starches: Isolationa nd Some Properties of Starches from *Cucurbit foetidissima* HBK and *Cucurbita digitata* Gray, J. Agric. Food Chem., vol. 23, No. 4, pp. 825–826 (1975).

M. Brusko, "He Tells EPA What To Do: Better Systems, fewer products are the key to safer, more profitable farming, this farmer says", The New Farm Magazine, Nov./Dec., pp. 11–16, (1989).

S. J. Castle, T. M. Perring, C. A. Farrar and A. N. Kishaba, "Field and Laboratory Transmission of Watermelon Mosaic Virus 2 and Zucchini Yellow Mosaic Virus by Various Aphid Species", The American Phytopathological Society, vol. 82, No. 2, pp. 235–240 (1992).

J. T. Alves Costa and W. P. Bemis, "After–ripening effect of seed germination and viability of *Cucurbita foetidissima* seed", reprinted from *Turrialba*, vol. 22, No. 2, pp. 207–209, (1972).

N. J. Daghir, H. K. Mahmound and A. El–Zein, "Buffalo Gourd *Cucurbita foetidissima*) Meal: Nutritive Value and Detoxification", Nutrition Reports International, vol. 21, No. 6, pp. 836–847 (1980).

A. David, D. K. Vallance, "Letters to the Editor: Bitter Principles of Cucurbitaceae", Astracts, pp. 295–297, (1955).

C. J. Deheer and D. W. Tallamy, "Affinity of Spotted Cucumber Beetle (Coleoptera: Chrysomelidae) Larvae to Cuburbitacins", Entomological Society of America, pp. 1173–1175, (1991).

J. C. Delouche, T. W. Still, M. Raspet and M. Lienhard, "The Tetrazolium Test for Seed Viability", Mississippi Agricultural Experiment Station Technical Bulletin, pp. 1–63, (1962).

M. L. Dreher, J. C. Scheerens, C. W. Weber and J. W. Berry, "Nutritional Evaluation of Buffalo Gourd Root Starch", Nutrition Reports International, vol. 23, No. 1, pp. 1–9, (Jan. 1981).

D. A. East, J. V. Edelson, E. L. Cox and M. K. Harris, "Evaluation of screening methods and search for resistance in muskmelon, *Cucumis melo* L. to the two–spotted spider mite, *Tetranychus urticae* Koch", Crop Protection, vol. 11, pp. 39–44 (Feb. 1992).

P. R. Enslin, "Bitter Principles of the Cucurbitaceae I. –Observations on the Chemistry of Cucurbitacin A", J. Sci. Food Agric. 5, pp. 410–416, ( Sep. 1954).

M. L. Dreher and J. W. Berry, "Buffalo Gourd Root Starch: Part I. Properties and Structure", Starch/Starke 35, Nr. 3, pp. 76–81 (1983).

M. L. Dreher, A. M. Tinsley, J. C. Scheerens and J. W. Berry, "Buffalo Gourd Root Starch: Part II. Rheologic Behavior, Freeze–thaw Stability and Suitability for Use in Food Products", Starch/Starke 35, Nr. 5, pp. 157–162 (1983).

J. E. Ferguson, D. C. Fischer and R. L. Metcalf, "A Report of Cucurbitacin Poisonings in Humans", CGC, 6:73–74, (1983).

J. E. Ferguson, R. L. Metcalf and D. C. Fischer, "Disposition and Fate of Cucurbitacin B in Five Species of Diabroticites", Journal of Chemical Ecology, vol. II, No. 9, pp. 1307–1321 (1985).

J. E. Ferguson and R. L. Metcalf, "Cucurbitacins Plant–Derived Defense Compounds for Diabroticites (Coleoptera: Chrysomelidae)", Journal of Chemical Ecology, vol. II, No. 3, pp. 311–319 (1985).

S. Gitter, R. Galilly, B. Shohat and D. Lavie, "Studies on the Antitumor Effect of Cucurbitacins", SBLI, pp. 516–521 (Oct. 1960).

J. Guha and S. P. Sen, "The Cucurbitacin–A Review", The Plan Biochemical Journal 2(1):12–28(1975).

J. F. Harrington, "Effect of Fruit Maturity and Harvesting Methods on Germination of Muskmelon Seed", American Society for Horticultural Science, vol. 73, pp. 422–430, (Oct. 1958).

B. T. Hawthorne, "Effects of cultural practices on the incidence of storage rots in *Cucurbita* spp.", New Zealand Journal of Crop and Horticultural Science, vol. 17:49–54 (1989).

D. Hest, "Rootworms May Die for Love Potion No. 9", The Farmer, 103(13):27(Aug. 1987).

A. D. Holmes, "Germination of Seeds Removed from Mature and Immature Butternut Squashes after Seven Months of Storage", American Society for Horticultural Science, v. 62, pp. 232–236(1953).

W. L. Howe, J. R. Sanborn and A. M. Rhodes, "Western Corn Rootworm Adult and Spotted Cucumber Beetle Associations with *Cucurbita* and *Cucurbitacins*", Environmental Entomology, vol. 5, No. 6, pp. 1043–1048(Dec. 1976).

H. E. Hummel and J. F. Anderson, "Secondary plant factors of Cucurbita species suppress sex attraction in the beetle Diabrotica under cimpunctata howardi", Proc. 5th int. Symp. Insect–Plant Relationships, Wageningen, pp. 163–167 (1982).

T. F. Hutt and M. E. Herrington, "The Determination of Bitter Principles in Zucchinis", J. Sci. Food Agric. vol. 36, pp. 1107–1112 (1985).

P. J. Hylands and A. M. Salama, "Cucurbitacin S. A New Cucurbitacin From Bryonia Dioica", Phytochemistry, vol. 15, pp. 559–560(1976).

P. J. Hylands and M. T. Oskoui, "3α–Hydroxy–Multiflora–7,9(11)–Dien–29α–OIC Acid, A New Triterpene from Bryonia Dioica", Phytochemistry, vol. 18, pp. 1843–1845 (1979).

P. J. Hylands, E. S. Mansour, M. T. Oskoui, "Bryocoumaric Acid, A New Triterpene from Bryonia dioica", reprinted from Journal of The Chemical Society, pp. 2933–2936 (1980).

P. J. Hylands and E. S. Mansour, "New Cucurbitacin Derivatives from Bryonia dioica Jacq.", J. Chem. Soc. Perkin Trans. I, pp. 2821–2825 (1983).

J. C. Kirschmann and R. L. Suber, "Letter to the Editor: Recent Food Poisonings from Cucurbitacin in Traditionally Bred Squash", Fd Chem. Toxic, vol. 27, No. 8, pp. 555–556 (1989).

D. R. Lance and G. R. Sutter, "Field–Cage Tests of Semichemical–Based Toxic Baits for Diabrotica Bettles: Effects of Particle Distribution and Attractant Content", (Mar. 1990).

D. R. Lance and G. R. Sutter, "Field–Cage and Laboratory Evaluations of Semiochemical–Based Baits for Managing Western Corn Rootworm (Coleoptera: Chrysomelidae)", Journal of Economic Entomolgy, vol. 83, No. 3, pp. 1085–1090 (Jun. 1990).

D. R. Lance and G. R. Sutter, "Semichemical–Based Toxic Baits for *Diabrotica virgifera virgifera* (Coleoptera: Chrysomelidae): Some Effects of Particle Distribution and Attractant Content", J. Econ. Entomol. Forage and Row Crops.

D. R. Lance and G. R. Sutter, "Field Tests of Semichemical–based Toxic Baits for Suppression of Corn Rootworm Beetles (Coleoptera: Chrysomeliadae)", J. Econ. Entomol. Forage and Row Crops, (Mar. 1991).

D. R. Lance and G. R. Sutter, "Semichemical–Based Toxic Baits for *Diabrotica virgifera virgifera*(Coleoptera: Chrysomelidae): Effects of Particle Size, Location, and Attractant Content", Journal of Economic Entomology, vol. 84, No. 6, pp. 1861–1868 (Dec. 1991).

J. R. Mason and T. Turpin, "Cucurbitacin–Adulterated Diet Is Avoided By Captive European Starlings", Cucurbitacins: J. Wildl. Manage 54:(4), pp. 672–676 (1990).

R. Mata, P. Castaneda, M. R. Camacho, "Chemical Studies on Mexican Plants Used in Traditional Medicine v. Cucurbitacin Glucosides From Cigarrilla, Mexicana", Journal of Natural Products, vol. 51, No. 5, pp. 836–839 (Sep.–Oct. 1988).

R. Mata, M. R. Camacho, E. Cervera, R. Bye and E. Linares, "Secondary Metabolites From Hintonia Latiflora", Phytochemistry, vol. 29, No. 6, pp. 2037–2040 (1990).

Lance J. Meinke, "1985 Adult Western Corn Rootworm Suppression Study Large Scale Griffin Formulation Evaluation", paper for Department of Entomology, University of Nebraska, Lincoln, Nebr., pp. 1–4 (1985).

L. J. Meinke, Z. B. Mayo and T. J. Weissling, "Pheromone Delivery System: Western Corn Rootworm (Coleoptera: Chrysomelidae) Pheromone Encapsulations in a Starch Borate Matrix", Journal of Economic Entomology, vol. 82, No. 6, pp. (Dec. 1989).

R. L. Metcalf, R. A. Metcalf and A. M. Rhodes, "Cucurbitacins as Kairomones for diabroticite beetles", Proc. Natl. Acad. Sci. USA, vol. 77, No. 7, pp. 3769–3772 (Jul. 1980).

R. L. Metcalf, A. M. Rhodes, R. A. Metcalf, J. Ferguson, E. R. Metcalf and P. Lu, "Cucurbitacin Contents and Diabroticite (Coleoptera: Chrysomelidae) Feeding upon *Cucurbita spp.*", Entomological Society of America, vol. 11, No. 4, pp. 931–937 (Aug. 1982).

R. L. Metcalf, J. E. Ferguson, D. Fischer, R. Lampmann and J. Anderson, "Controlling Cucumber Beetles and Corn Rootworm Beetles with Baits of Bitter Cucurbit Fruits and Root", CGC 6:79–81 (1983).

Robert L. Metcalf, "Coevolutionary Adaptations of Rootworm Beetles (Coleoptera: Chrysomelidae) to Cucurbitacins", Journal of Chemical Ecology, vol. 12, No. 5, (1986).

R. L. Metcalf, J. E. Ferguson, R. Lampman and J. F. Anderson, "Dry Cucurbitacin–containing Baits for Controlling Diabroticite Beetles (Coleoptera: Chrysomelidae)", Journal of Economic Entomology, vol. 80, No. 4, pp. 870–874 (Aug. 1987).

R. L. Metcalf and R. L. Lampman, "The Chemical Ecology of Diabroticites and Cucurbitaceae", Experientia 45, pp. 240–247 (1989).

Daniel E. Moerman, "Medicinal Plants of Native America", University of Michigan Museum of Anthropology Technical Reports, No. 19 (1986).

C. A. Mullin, Ali A. Alfatafta, J. L. Harman, S. L. Everett and A. A. Serino, "Feeding and Toxic Effect of Floral Sesquiterpene Lactones, Diterpenes, and Phenolics from Sunflower (*Helianthus annuus* L) on Western Corn Rootworm", Journal of Agricultural and Food Chemistry, vol. 39, No. 12, pp. 2293–2299 (1991).

Gary Nabhan and Jill Thompson, "Wild Cucurbita in Arid America: Ethnic Uses, Chemistry and Geography", Native Seeds/Search, pp. 1–20 (1985).

J. M. Nelson, J. C. Scheerens, J. W. Berry and W. P. Bemis, "Effects of Plant Population and Planting Date on Root and Starch Production of Buffalo Gourd Grown as an Annual", J. Amer. Soc. Hort. Sci. 108(2):198–201 (Mar. 1983).

J. M. Nelson, J. C. Scheerens, T. L. McGriff and A. C. Gathman, "Irrigation and Plant Spacing Effects on Seed Production of Buffalo and Coyote Gourds", Agronomy Journal, vol. 80, No. 1, pp. 60–65 (1988).

J. M. Nelson, J. C. Scheerens, D. A. Bucks and J. W. Berry, "Irrigation Effects on Water Use, and Production of Tap Roots and Starch of Buffalo Gourd", Agronomy Journal, vol. 81, No. 3, pp. 439–442 (1989).

John Nelson, "The Buffalo Gourd–Information on its Culture for Root and Seed Production", paper for University of Arizona, Maricopa Agricultural Center, pp. 1–6 (Jan. 1991).

R. Nishida and H. Fukami, "Sequestration of Distasteful Compounds By Some Pharamcophagous Insects", Journal of Chemical Ecology, vol. 16, No. 1, pp. 151–164 (199).

Jane Paul, "Getting Tricky With Rootworms: Here's a twist on the old bait–and –switch game", Agrichemical Age, pp. 6, 25E, and 30 (Mar. 1989).

T. M. Perring, C. A. Farrar, K. Mayberry and M. J. Blua, "Research Reveals Pattern of Cucurbit Virus Spread", California Agriculture, vol. 46, No. 2, pp. 35–40 (Apr.–Mar. 1992).

M. Pitrat, "Linkage Groups in *Cucumis melo L.*", Journal of Heredity, 82:406–411 (1991).

D. R. Raemisch and F. T. Turpin, "Field Tests For An Adult Western Corn Rootworm Aggregation Pheromone Associated with the Phagostimulatory Characteristic of Bitter *Cucurbita spp.*,", J. Agric. Entomol. 1(4):339–344 (Oct. 1984).

S. Rehm, P. R. Enslin, A. D. J. Meeuse and R. H. Wessels, "Bitter Principles of the Cucurbitaceae. VII.—The Distribution of Bitter Principles in this Plant Family", J. Sci. Food Agric., pp. 679–686 (Dec. 1957).

A. M. Rhodes, R. L. Metcalf and E. R. Metcalf, "Diabroticite Beetle Responses to Cucurbitacin Kairomones in *Cucurbita* Hybrids", J. Amer. Soc. Hort. Sci. 105(6):838–842 (1980).

K. S. Rymal, O. L. Chambliss, M. D. Bond and D. A. Smith, "Squash Containing Toxic Cucurbitation Compounds Occurring in California and Alabama", Journal of Food Protection, vol. 47, pp. 270–271 (Apr. 1984).

S. M. Sakr and E. E. Mahmoud, "Viability of Seeds Harvested from Fruits at Different Stages of Maturity", American Society for Horticultural Science, pp. 326– 329 (1952).

J. C. Scheerens and J. W. Berry, "Buffalo Gourd: Composition and Functionality of Potential Food Ingredients", Cereal Foods World, vol. 31, No. 2, pp. 183–192 (Feb. 1986).

G. C. Sharma and C. V. Hall, "Influence of Cucurbitacins,

Sugars, and Fatty Acids on Cucurbit Susceptibility to Spotted Cucumber Beetle", J. Amer. Soc Hort. Sci. 96(5):675–680 (1971).

G. S. Stoewsand, A. Jaworski, S. Shannon and R. W. Robinson, "Toxicologic Response in Mice Fed Cucurbita Fruit", Journal of Food Protection, vol. 48, No. 1, pp. 50–51 (Jan. 1985).

H. Stuppner and H. Wagner, "New Cucurbitacin Glycosides from *Picrorhiza kurrooz*", Planta Medica 55, pp. 559–563 (1989).

G. R. Sutter and D. R. Lance, "New Strategies for Reducing Insecticide Use in the Corn Belt", Sustainable Agriculture Field Research and Education, pp. 231–249 (1991).

Douglas W. Tallamy, "Squash Beetle Feeding Behavior: An Adaptation Against Induced Cucurbit Defenses", Ecology, 66(5) pp. 1574–1579 (Oct. 1985).

D. W. Tallamy and V. A. Krischik, "Variation and Function of Cucurbitacins in *Cucurbita*: An Examination of Current Hypotheses", The American Naturalist, vol. 133, No. 6, pp. 766–786 (Jun. 1989).

D. W. Tallamy and E.S. McCloud, "Squash Beetles, Cucumber Beetles, and Inducible Cucurbit Responses", Phytochemical Induction By Herbiores, pp. 155–181 (1991).

T. J. Weissling and L. J. Meinke, "Potential of Starch Encapsulated Semiochemical/Insecticide Formulations for Adult Corn Rootworm (Coleoptera: Chrysomelidae) Control", Journal of Economic Entomology, Forage and Row Crops, pp. 1–36 (87/89).

T. J. Weissling, "Behavioral Responses of *Diabrotica* Adults to Plant–Derived Semichemicals Encapsulated in a Starch Borate Matrix", Entomol. Exper. Appl. vol. 1, 53:219–228 (Aug. 1990).

T. J. Weissling, L. J. Meinke, D. Trimmell and K. L. Golden, "Behavioral Responses of *Diabrotica* Adults to Plant–Derived Semiochemicals Encapsulated in a Starch Borate Matrix, Entomol. Exp. Appl. 53:219–228 (1989).

T. J. Weissling and L. J. Meinke, "Potential of Starch Encapsulated Semiochemical– Insecticide Formulations for Adult Corn Rootworm (Coleoptera: Chrysomelidae) Control", Entomological Society of America, vol. 84, No. 2, pp. 601–609 (Jul. 1991).

T. J. Weissling, L. J. Meinke and K. A. Lytle, "Effect of Starch–Based Corn Rootworm (Coleoptera: Chrysomelidae) Baits on Selected Nontarget Insect Species: Influence of Semiochemical Composition", Entomological Society of America, vol. 84, No. 4, pp. 1235–1241 (Aug. 1991).

T. J. Weissling and L. J. Meinke, "Semiochemical–Insecticide Bait Placement and Vertical Distribution of Corn Rootworm (Coleoptera: Chrysomelidae) Adults: Implications for Management", Entomological Society of America, vol. 20, No. 3, pp. 945–952 (Jun. 1991).

Robert E. Young, "The Effect of Maturity and Storage on Germination of Butternut Squash Seed", American Society For Horticultural Science, vol. 53, pp. 345–347 (1949).

P. Yang, S. Liu, Z. Coa, W. Chang and C. Che, "Cucurbitacin Contents in *Hemsleya dolichocarpa*, *"American Journal of Chinese Medicine, vol. XIX, No. 1, pp. 51–56 (1991)*.

Trimnell et al., "Pesticide Encapsulation Using a Starch–Borate Complex as Wall Material", *J. Appl. Poly. Sci.*, vol. 27, 3919–3928 (1982).

Dunkle et al, "Starch–Encapsulated *Bacillus thuringiensis*: A Potential New Method for Increasing Environmental Stability of Entomopathogens", Environ. Entom., vol. 17, No. 1, 120–126 (1988).

Tollefson, "Treatment of Adult Corn Rootworms with a Semiochemical and Insecticide Mixture to Disrupt Oviposition and Subsequent Larval Damage" (1984).

Tollefson, "Control of Western Corn Rootworm Larvae Through Adult Suppression" (1985).

5,484,587

DIABROTICINE BAIT

FIELD OF THE INVENTION

The invention relates to a bait having a particularly effective form and structure for control of diabroticine larvae and beetles.

BACKGROUND OF THE TECHNOLOGY

Diabroticine beetles are a significant problem during the growth of, inter alia, corn (field, pop, seed, and sweet), beans, Cucurbitaceae (including cucumbers, melons, squash, and pumpkins), peanuts, peas, potatoes, and sweet potatoes. Corn is conveniently used to describe the effects of diabroticine beetles. These pests are the direct or indirect (i.e., as a vector for bacteria and inoculation of melons and squash) cause of millions of dollars of crop and garden damage annually. Damage by these beetles has continued despite over 30 years of attempts at control.

Diabroticine beetles encompass multivoltine and univoltine species. Multivoltine species (e.g., the southern corn rootworm) can produce up to 3 generations a year. Univoltine species (e.g., northern and western corn rootworm) have a life cycle that starts with eggs laid 4–24 inches below the soil in the Fall. In early Spring and over the course of several weeks, the larvae hatch and begin to feed on nearby roots thereby destroying the root's anchoring abilities and the microhairs responsible for mineral, nutrients, and water assimilation. If the plant roots have not been so damaged that the plants falls over, the yield from the affected plants is reduced due to impaired nutrition.

After feeding, the diabroticine larvae pupate and emerge from the ground as adult beetles. Univoltine beetles emerge at some time during mid July through August (depending on local climate). Male diabroticine beetles emerge about 1 week before the females (week 1) which, in turn, emerge at about the same time as corn silks emerge. Because the fresh silks emit a number of volatile agents which are attractive to both the male and female beetles, the 7–10 days of silking represents a period of high feeding activity for the beetles. The beetles immediately begin to migrate up the stalk toward the leaves, ears, and silks. This compulsion is quite strong since there is evidence that the beetles will not move down the corn stalk in response to attractants. Throughout this period, the beetles feed and mate.

The key to control of the diabroticine beetles is to disrupt the life cycle by affecting the larvae and/or adult beetles. One method known in the art as "banding" refers to the practice of trying to control the larvae by applying a contact insecticide in or along a furrow containing planted seeds. The theory behind banding is that larvae will enter the treated area when searching for roots and die due to contact with the insecticide.

Unfortunately, microbial attack impairs the efficacy of the insecticides well before all the larvae have had time to hatch and, enter the band. Additionally, concerns for groundwater contamination. The impact on nontarget organisms (e.g., bird kill), and the hazards of human exposure to the toxic insecticides restrict the use of insecticides that might survive the effects of microbial attack during the larval feeding stage. Moreover, plant roots often extend well beyond the band leaving the roots vulnerable to attack.

Recently, it has been proposed to use the tissue of dried gourds from the Cucurbitale order in combination with 0.01–10% by weight of an insecticide to make a lethal bait for the control of diabroticine beetles. From Canadian Patent No. 1,195,922, the bitter tasting gourd tissue acts as a compulsive feeding stimulant for diabroticine beetles but does not harm beneficial insects. By coating the gourd tissues with an insecticide, the beetles compulsively consume a lethal quantity of insecticide. From the examples in the patent, gourd fruits were dried and ground in a food processing mill to 30–60 mesh (250–550 micron diameter), surface coated with an insecticide solution, and broadcast over the tops of sweetcorn plants at 10–100 lbs. per acre. The bait was reported to be effective at killing diabroticine beetles for at least two weeks. Later developments in U.S. Pat. No. 4,880,624 reported an increased level of efficacy when the composition is mixed with volatile attractants.

Notwithstanding the promising results obtained by the use of a compulsive feeding stimulant, there remains room for even higher levels of diabroticine control.

SUMMARY OF THE INVENTION

It is an objective of the invention to provide a bait and method of use therefor having high levels of diabroticine control.

It is another objective of the invention to provide a composition containing an intimate admixture of a compulsive feeding stimulant and insecticide in a form useful for application as a solid or from a suspension in a liquid with components that are palatable to the diabroticine.

In accordance with these and other objectives that will become apparent from the description herein, compositions according to the invention comprise:

a bait for diabroticine larvae and beetles comprising particles containing an amount of a cucurbitacin-containing material admixed with a diabroticidal insecticide in a binding agent comprising a gelatin and a gum.

The invention provides a high rate of kill in adult diabroticine beetles at low material application rates. The present invention also reduces the effects of nontarget organism impact and human exposure when applying toxicants to the soil in banding for the control of diabroticine beetle larvae. Accordingly, the amount of insecticide released into the environment can be substantially reduced while providing effective levels of control. Improved control over diabroticine beetle infestations enables those growing crops susceptible to diabroticine attack to begin reducing diabroticine populations to an economic level while protecting beneficial insects.

DETAILED DESCRIPTION

Figure 1:
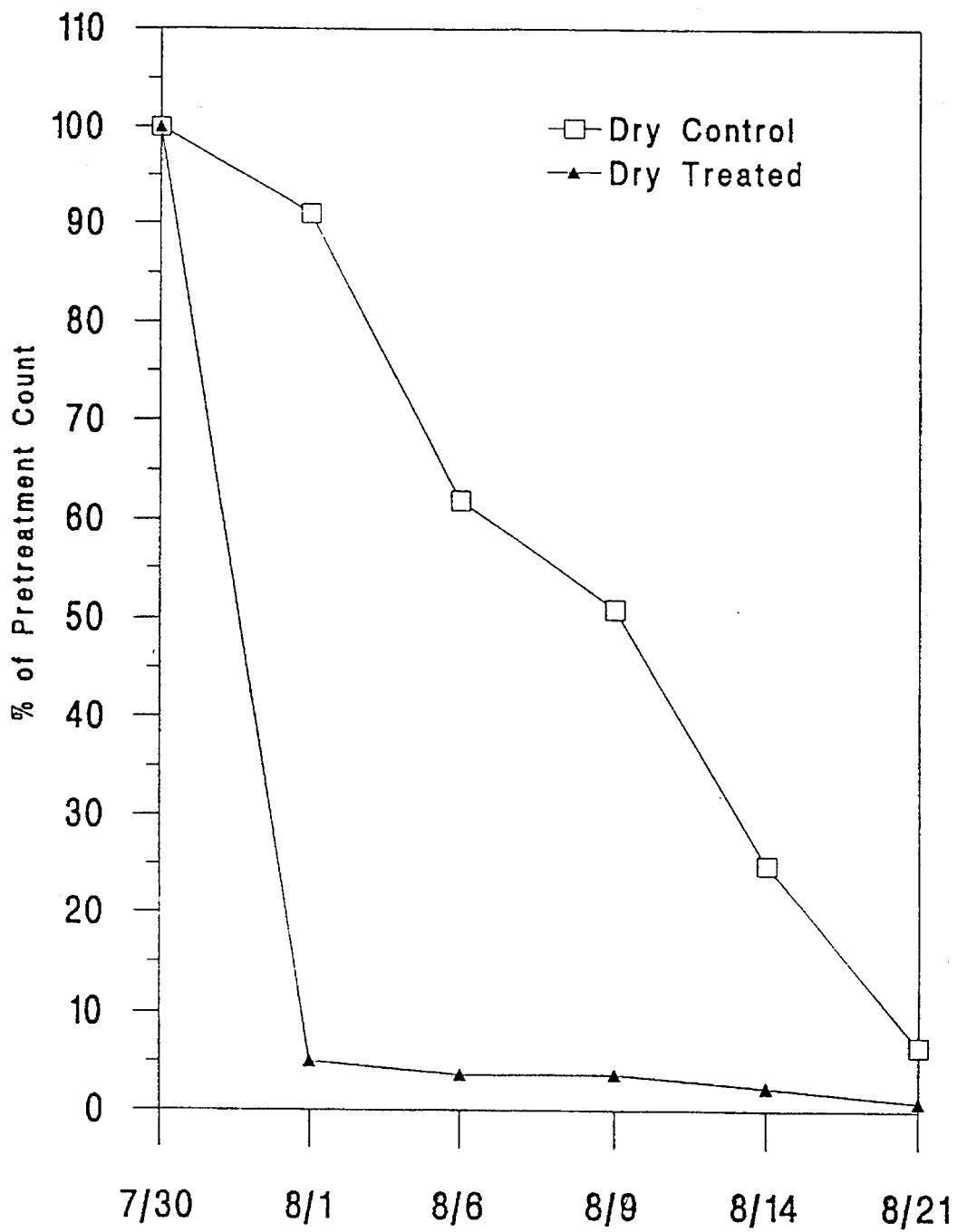
FIG. 1 is a graph showing the control afforded by the present invention over western corn rootworm in dry fields.

The present invention controls diabroticine infestation in a variety of plants using cucurbitacin-containing material intimately associated with a diabroticine insecticide. Plants that can be protected according to the present invention include virtually any plant affected by diabroticine beetles. Examples of such plants include, inter alia, corn (field, pop, seed, and sweet), beans, Cucurbitaceae (including cucumbers, melons, squash, and pumpkins), peanuts, peas, potatoes, and sweet potatoes.

Diabroticine beetles that are controlled in accordance with the invention include the banded cucumber beetle (*Diabrotica balteata*), the green maize beetle (*Diabrotica decolor*), the twelve-spotted cucumber beetle (*Diabrotica duodecimpunctata*), the northern corn rootworm (*Diabrotica barberi*), the southern corn rootworm or spotted cucumber beetle (*Diabrotica undecimpunctata howardi*), the western spotted cucumber beetle (*Diabrotica undecimpunctata undecimpunctata*), the western corn rootworm (*Diabrotica virgifera virgifera*), the striped cucumber beetle (*Acalymma vittata*), Western striped cucumber beetle (*Acalymma trivittata*), the Mexican corn rootworm (*Diabrotica virgifera zeae*), *Diabrotica adelpha, D. speciosa speciosa, D. speciosa vigens, D. viridula, D. cristata, D. undecimpunctata sensulato, D. undecimpunctata tenella*, and *D. undecimpunctata duodecimnotata*. Each of these beetles has evolved to compulsively consume plant tissue of the cucurbitale order. The cucurbitacins in these tissues are strongly bitter and detectable by humans at rates as low as 1 part per billion. When consumed by diabroticine beetles, the cucurbitacins are sequestered in the wings thereby acting as a predation deterrent.

The cucurbitacin-containing plants useful in the present invention as feeding stimulants are well described in Canadian Patent No. 1,195,922, U.S. Pat. No. 4,880,624, and *The Merck Index*, 10th ed., p. 2609 (1983). Briefly summarized, plants in the cucurbitacae order contain small quantities of oxygenated tetracyclic triterpenoid compounds (usually referred to as the cucurbitacins) that are responsible for the bitter taste of the plant tissue. Seventeen of the cucurbitacins have been isolated and identified by letters. If desired, diluted synthetic cucurbitacin may be made and carried on a particulate carrier. References herein the "cucurbitacin-containing" shall mean plant tissues or carriers containing at least one of the cucurbitacins A, B, C, D, E, F, G, H, I, J, K, L, O, P, Q, R, or glycosides of any of these. Materials containing the E and/or E glycoside cucurbitacins are preferred.

Plant tissues containing the highest levels of cucurbitacins include the roots of the buffalo gourd (*Cucurbita foetidissima*) which, when dried, contain about 0.3% by weight cucurbitacins. Other cucurbitan-containing materials useful for the invention may come from, inter alia, *C. andreana* NAUD, *C. cylindrata* Wats, *C. ecuadorensis* Cutl. and Whit., *C. foetidissima* HBK, *C. gracilior* Bailey, *C. lundelliana* Bailey, *C. martinezii* Bailey, *C. okeechobensis* Bailey, *C. palmata* Wats., *C. palmeri* Bailey, *C. pedatifolia* Bailey, *C. sororia* Bailey, and *C. texana* Gray.

Buffalo gourd root powder is the preferred source of cucurbitaacin-containing material for use as the feeding stimulant component in baits of the invention because the root powder contains a significant quantity of starch. This starch acts as a sticking agent when wetted to assist the applied particle in adhering to the plant surface. Such adhesion properties are advantageous when bait particles are aerially applied.

The use of cucurbitacin-containing plant tissues has a number of practical benefits. First, the inherent chemical composition of cucurbitacin-containing plant tissue is responsible for the compulsive feeding effects. Cucurbitacin-containing plant tissues can, therefore, be used in a dry form which reduces the special handling and storage concerns with grinding, formulating, and storing moist plant tissues. Moreover, the stimulation effects are found at such extremely low levels that there are no special handling procedures for handling the cucurbitacin which is quite toxic in its pure form. Only the insecticides might require special handling.

Diabroticidal insecticides useful for the invention are those effective to control the diabroticine population by killing or sterilizing diabroticine larvae or beetles. Insecticides having diabroticidal activity and useful in the present invention include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, and phosmet); compounds which break down the beetle's digestive tract tissue including fluorine compounds (cryolite), zinc, and mercury; nicotine; rotenone; neem oil or azadoractin; natural or synthetic pyrethrins; petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); Bacillus thuringiensis; and diabroticidal viruses (e.g., entomopathic viruses such as bacculo). Most of these insecticides are commercially available in the form of a solid particle. Liquids may be used although the use of microencapsulated liquids or fine solids coated with cucurbitacin-containing material are preferred for handling and control over the released volatiles. The carbamates are preferred with carbaryl and methomyl being most preferred.

If desired, the baits may contain one or more attractants for diabroticine beetles. Attractants such as those in U.S. Pat. No. 4,880,624 (herein incorporated by reference) are preferred.

Baits of the invention contain sufficient cucurbitacin-containing material to stimulate compulsive feeding in cliabroticine beetles in intimate association with sufficient diabroticidal insecticide to effect control over the population of the beetles. Baits can contain 0.01–99 wt % cucurbitaacin-containing material and 0.01–99 wt % insecticide. Preferably, the baits contains at least 50 wt % cucurbitacin-containing material and less than 50 wt % insecticide. Even more preferable, the baits contain 0.01–25 wt % insecticide with the remainder cucurbitacin-containing material and any additives or attractants. Examples of additives useful in the present invention include preservatives (e.g., sodium benzoate), plasticizers (e.g., sorbitol, maltodextrin), food starch, gums (sodium carboxymethylcellulose, carrageenan, and gellan), and gelatin (e.g., pork gelatin).

In the present invention, the feeding stimulant component of the bait is presented on the outside surface of the bait particle. A preferred method for making the present microspherical particles is to grind the cucurbitacin-containing material and a solid diabroticine insecticide to a fine particle size of about 8–20 μm, mix these powders with appropriate binding agents until homogeneous, and spray dry the mixture into a finely divided microsphere bait. Appropriate control over the spray drying nozzle size and conditions permit a controlled particle size distribution effective to spray or broadcast the particles over the upper surface of the plants to be protected or anywhere along the travel path of diabroticine beetles. Suitable sizes are less than 1000 μm in bait diameter, preferably less than 600 μm in diameter. Particularly effective particle sizes are when 100% of the bait particles exhibit a diameter of less than 200 μm with a high rate of acceptance if the particle diameters are 100% less than 100 μm in diameter. In this form, consumption of the cucurbitacin-containing material will necessarily involve consumption of the insecticide. It should be noted that use of the phrase generally "microsphere" is intended to note a small, generally rounded particle that exhibits a shape formed from surface tension effects which may not be mathematically spherical.

An alternative to a homogeneous microsphere bait particle is a similarly dimensioned microcapsule with a central core comprising insecticide that is substantially covered by an outer layer comprising or consisting essentially of cucurbitacin-containing material. Preferably, the outer layer does not contain appreciable quantities of insecticide. Such microcapsules can be made with conventional coextrusion encapsulation techniques.

Care should be exercised in selecting binder components when the bait is to be formed into microspheres or microcapsules. The materials must be palatable to the beetles, adhere to the plant foliage while resisting washoff and weathering, and resist molds and decay. At the present time, a preferred formulation comprises 1.5–3 wt % carrageenan gum, 12–15 wt % pork gelatin, 3–6 wt % sorbitol, 0.05–0.2 wt % sodium benzoate, 14–18% carbaryl, and 62–67 wt % buffalo gourd root powder. Starch in the root powder acts as a sticking agent which reduces the need for the addition of external sticking agents. If other sources of cucurbitacin are used, an added sticking agent may be needed to achieve satisfactory levels of adhesion to the plant surfaces particularly when the particles are deposited on the plant by aerial spraying.

Another form of bait that will present an outer covering of feeding stimulant is a solid insecticide particle that has been coated at least in part (preferably, it is completely covered) with a finely ground cucurbitacin-containing material. Preferably at least 10% of the outer surface area of the insecticide particle is covered with cucurbitacin-containing material dust or particles. Such a bait is useful to enhance the efficacy of traditional diabroticine beetle larvacides for when these are applied to the soil in or along at least one side of a furrow containing seed in the practice known as banding. In banding, an applicator mixes buffalo gourd root powder in the application tank with an aqueous or corn oil suspension of insecticide granules or wettable powder and applies the modified insecticide bait particle according to conventional banding practice and rates. It should be noted that birds and other animals that might feed on the banded granules will be deterred from consuming the particles from the bitter initial taste of the cucurbitacins. The preferred form of bait, however, is a microsphere that intimately binds the feeding stimulant to the insecticide.

When used as an adulticide, the baits exhibit a surprisingly high level of diabroticine control while enabling the application of overall lower levels of insecticide relative to conventional practice. For example, the currently approved application rate for control of diabroticine beetles by carbaryl is 454–908 g active carbaryl/acre. With the present invention, however, the higher levels of control are realized by a significantly lower application rate. For carbaryl, this rate is within the range from about 5 to about 200 g active ingredient (AI)/acre, preferably about 5–100 g AI/acre, and most preferably about 20–50 g AI/acre. Practical carbaryl formulations will translate into an application rate of 5–20 lbs. of bait per acre when formed as a dry granule using an inert carrier (such as corn cob grit or clay) or 4–25 ounces of suspended microspheres per acre.

The quantities of diabroticidal insecticides other than carbaryl are used in quantities proportional to their diabroticidal efficacy relative to the levels of carbaryl used herein. As an example, diabroticidal insecticides that are 50% as effective as carbaryl are used in quantities of 10–400 g AI/acre, but insecticides that are twice as effective are used in quantities within the range from about 2.5–100 g AI/acre. The precise application rate of any particular insecticide when supplied in a microsphere or microcapsule form is readily determinable by one in this art with the exercise of no more than the existing skill level after consideration of the present disclosure.

As adulticides, bait particles of the present invention are applied to the plant surfaces just before emergence of the adult diabroticine beetles or when counts indicate a level of infestation of about 0.5–1 beetles per plant. If this level of infestation is not achieved, commercial fields are not considered to be economically justified for treatment because the losses sustained by beetle damage are worth less than the cost of an average treatment.

At 7–10 days after first emergence of the adult beetles, the beetle population will be at its peak. Baits of the present invention should on the plants by this time and remain available for the next week. This timing and duration maximize the control over beetles that will produce the progeny causing the succeeding year's root damage.

Dry particles or a liquid suspension of the bait particles are distributed over the tops of the plants to be treated by conventional ground or aerial spraying and equivalent methods. The objective of such application methods is to deposit bait particles on the upper surfaces of the plant leaves, silks, and whorls where the diabroticine beetles will locate them while foraging for food.

One method for applying dry bait particles that has proven to be acceptable is to load dry corn cob grit having a size of 40–60 mesh (250–360 μm) with spray dried microsphere bait particles according to the invention. These corn cob particles have an open network of pores that will readily hold fine bait particles such as those of the invention yet present a sufficiently large particle size that the grit particles can be applied aerially without experiencing significant amounts of lost material due to bouncing off the plant surfaces upon landing. Preferably, porous carriers for the present bait particles have a bulk density of about that of corn cob grit. In practice, it has been found that the diabroticine beetles will consume bait particles from within the openings of the grit or those that have fallen out as a result of landing on the plant surface. Either mode of consumption results in a high rate of kill.

When used as a larvacide, baits are applied to the soil in a furrow containing plant seeds or along at least one of the sides of the seed-containing furrow in a rate corresponding to about 400 grams of active insecticidal ingredient per acre or less. Preferably, the baits are applied in the same manner as the conventional practice of banding at a rate within the range from about 100 to about 200 grams of active diabroticidal insecticide per acre. Larvae will feed on the cucurbitacin (see, Deheer et al., *Environ. Entomol.*, 20(4), pp 1173–1175 (1991)) and, due to the structure of the bait, consume or contact a lethal quantity of the associated insecticide.

Examples

The following examples are useful to understand the present invention.

Examples 1–6

Samples having the proportions in Table 1 were prepared by dissolving the gelatin, carrageenan gum, sorbitol, sodium benzoate, and any food starch in water at 82° C. (180° F.). The solution was cooled to 60° C. (140° F.) and maintained at a pH of 5–6. Thereafter, carbaryl and ground root powder were dispersed and mixed until homogeneous. Thereafter, the materials were spray dried to form microspheroidal particles having a particle size between about 50 µm and 100 µm. The inlet temperature of the spray drier was 180° C., and the outlet temperature was 90° C. The spray had a flow rate of 10 g/minute at a pressure of 25 psig.

The samples were tested in a conventional laboratory bioassay test. The bait was suspended in corn oil and sprayed on the upper surfaces of test corn plants. Table 1 lists the average number of dead beetles found on each plant after an exposure of 18 hrs. to an environment containing 15 diabroticine beetles. Sample 2 is, however, an aged sample that was 24 hrs old before application and exposed on the plant for 20 hrs. Each sample was replicated 3 times. The results are an average of those replications.

TABLE 1

| Material (in % of total weight) | 1 | 2 (sample aged 24 hrs) | 3 | 4 | 5 | 6 |
|---|---|---|---|---|---|---|
| Gelatin (pork source) | 15.5 | 15.5 | 15 | 20 | 22.2 | 16.7 |
| Sorbitol | 5.2 | 5.2 | | 5 | 11.1 | |
| Modified food starch | | | 10 | | | |
| Carrageenan | 1.6 | 1.6 | | | | |
| Sodium benzoate | 0.1 | 0.1 | 0.1 | 0.1 | 0.1 | 0.1 |
| Buffalo Gourd Root Powder | 64.7 | 64.7 | 62.4 | 62.4 | 55.5 | 69.3 |
| Carbaryl | 10.3 | 10.3 | 10.0 | 10.0 | 8.9 | 11.1 |
| Avg. Dead | 14.3 | 13 | 12.7 | 12.3 | 12 | 12 |
| % Mortality | 96 | 87 | 84 | 82 | 80 | 80 |

Examples 1–6 illustrate the increase in mortality rates with an increase in cucurbitacin content (Examples 1, 4, and 5) and the effect of differences in formulation on beetle acceptance.

As a comparative example, buffalo gourd root powder and carbaryl ground to a size of 10–20 μm were suspended in corn oil and tested in parallel with examples 1–6. The mortality rate of the suspended particles was 98% (avg. dead was 14.7) after an exposure of 18 hours. The formulation was unstable, however, and separated into a thick paste of particles at the bottom of the corn oil. Such separation properties would dramatically increase the difficulties associated with shipping and storing a commercial product. Moreover, the corn oil suspension exhibited an efficacy period of only about 3 days even under dry conditions. The microspheres did not have the separation problems of the fine particles and exhibited an efficacy period of up to about 14 days under the same conditions.

Example 7

Example 7 is a modified version of example 1. The bait of example 7 contained the materials listed in Table 2 and exhibited a particle size of 50–100 μm.

TABLE 2

| Component | Weight % of total | Weight (mg/g microsphere) |
|---|---|---|
| Gelatin (pork source)[1] | 13.3 | 133 |
| Sorbitol | 4.5 | 45 |
| Carrageenan[2] | 1.4 | 14 |
| Sodium benzoate | 0.1 | 1 |
| Carbaryl[3] | 16.1 | 161 |
| Buffalo Gourd Root Powder | 64.7 | 647 |

[1]710 Dee-Gee Gelatin ™
[2]Gelcarin GP 812 ™
[3]Carbaryl 80-W ™ containing 80% active material The bait of example 7 was applied to test fields of corn in Nebraska. From each field, 48–96 plants were sampled. All fields had pretreatment counts of western corn rootworm beetles which were above the economic threshold for treatment. At the time of treating, 10% of the females were gravid, and the crop was in early milk stage.

The fields were treated by dispersing the bait in water and aerially broadcast in 40 foot swaths at a rate of 0.75 lb. microspheres per acre. This application rate translates into 0.1 lb. active carbaryl per acre. Striped plots were treated by interspersing a treated swath with an untreated swath. Therefore, the striped plots received half of the regular application rate, i.e., the striped plots received 0.375 lb/acre microspheres (0.05 lb/acre active carbaryl). Table 3 lists the conditions for each field.

TABLE 3

| Field No. | No. of Acres | Irrigated or Dry | Broadcast or Strip | Application Date |
|---|---|---|---|---|
| 1 | 10 | D | — | Untreated control |
| 2 | 12 | D | — | Untreated control |
| 3 | 56 | D | B | 8/2 |
| 4 | 15 | D | B | 8/1 |
| 5 | 30 | D | S | 8/1 |
| 6 | 12 | D | S | 8/1 |
| 7 | 15 | I | — | Untreated control |
| 8 | 125 | I | S | 8/1 |
| 9 | 40 | I | B | 8/2 |

Tables 4 and 5 report the results of monitoring the western corn rootworm (W), northern corn rootworm (N), and ladybug adults and larvae (L) in terms of the average number of beetles per plant. The ladybug count is used as a measure of the effects of the toxicant on beneficial insects. Low levels of impact on beneficials is, of course, desirable. It should be noted that only the western corn rootworm counts were at a level considered to be economically justified in treating and reasonably susceptible to mathematic treatment.

TABLE 4

| Field | 7/26 (Before treatment) | | | 7/30 (Before Treatment) | | | 8/1 ... 3–6 hrs After Treatment | | | 8/1 ... 24 hrs After Treatment | | |
| --- | --- | --- | --- | --- | --- | --- | --- | --- | --- | --- | --- | --- |
| | W | N | L | W | N | L | W | N | L | W | N | L |
| 1 | 1.9 | 0.9 | 0.5 | 1.6 | 0.3 | 0.2 | — | — | — | 1.8 | 0.8 | 0.2 |
| 2 | 2.0 | 0.06 | 0.19 | 2.3 | 0.17 | 0.25 | — | — | — | 1.8 | 0.33 | 0.37 |
| 3 | 2.4 | 0.9 | 0.5 | 2.3 | 0.4 | 0.8 | 0.1 | 0.1 | 0.1 | 0.1 | 0.08 | 0.2 |
| 4 | 2.7 | 0.7 | 0.1 | 2.3 | 0.6 | 0.2 | — | — | — | 0.17 | 0.4 | 0.1 |
| 5 | 1.6 | 0.4 | 0.7 | 2.2 | 0.6 | 0.7 | — | — | — | 0.1 | 0.08 | 0.14 |
| 6 | 2.5 | 0.6 | 0.35 | 1.9 | 1.0 | 0.11 | — | — | — | 0.09 | 0.21 | 0.03 |
| 7 | — | — | — | 3.06 | 0.88 | 0.19 | — | — | — | 2.0 | 0.8 | 0.19 |
| 8 | 1.9 | 0.08 | 0.25 | 1.9 | 0.36 | 0.2 | — | — | — | 0.26 | 0.21 | 0.14 |
| 9 | 1.6 | 1.8 | 0.08 | 1.5 | 0.7 | 0.17 | 0.08 | 0.17 | 0.06 | 0.14 | 0.12 | 0.2 |

TABLE 5

| Field | 8/6 (5 days after treatment) | | | 8/9 | | | 8/14 | | | 8/21 | | |
| --- | --- | --- | --- | --- | --- | --- | --- | --- | --- | --- | --- | --- |
| | W | N | L | W | N | L | W | N | L | W | N | L |
| 1 | 1.1 | 0.25 | 0.08 | 0.9 | 0.6 | 0.2 | 0.35 | 0.12 | 0.15 | 0.16 | 0.04 | 0.19 |
| 2 | 1.35 | 0.17 | 0.25 | 1.1 | 0.23 | 0.14 | 0.6 | 0.2 | 0.14 | 0.1 | 0 | 0.08 |
| 3 | 0.1 | 0.08 | 0.1 | 0.08 | 0 | 0.1 | 0.08 | 0.04 | 0.2 | 0.04 | 0.02 | 0.08 |
| 4 | 0.06 | 0.04 | 0.14 | 0.08 | 0.06 | 0.06 | 0.06 | 0.04 | 0.3 | 0 | 0.02 | 0.06 |
| 5 | 0.08 | 0.07 | 0.14 | 0.09 | 0.07 | 0.14 | 0 | 0 | 0.12 | 0.02 | 0 | 0.12 |
| 6 | 0.05 | 0.06 | 0.13 | 0.08 | 0.05 | 0.15 | 0 | 0 | 0.08 | 0 | 0 | 0.08 |
| 7 | 1.7 | 0.37 | 0.23 | 2.4 | 0.6 | 0.46 | 1.6 | 0.6 | 0.2 | 0.02 | 0 | 0.08 |
| 8 | 0.05 | 0.05 | 0.2 | 0.13 | 0.08 | 0.16 | 0.02 | 0 | 0.08 | 0 | 0 | 0.02 |
| 9 | 0.1 | 0.02 | 0.23 | 0.17 | 0.04 | 0.17 | 0.02 | 0.04 | 0.19 | 0.02 | 0.02 | 0.02 |

Table 6 summarizes the western corn rootworm data from Tables 4 and 5 in conventional terms of an acreage-weighted average of mean plant beetle counts relative to the same field counts on 7/30 before treatment. The untreated control fields were contiguous to the treated fields and are used to gauge the local beetle population and the date when effects other than treatment begin to exert a dominating effect. From this average, the impact or control afforded by the invention is readily discerned.

TABLE 6

| | Western Corn Rootworm Summary | | | | | | |
| --- | --- | --- | --- | --- | --- | --- | --- |
| | 7/30 Pre-treatment | 8/1 (3 hr) | 8/1 (24 hr) | 8/6 | 8/9 | 8/14 | 8/21 |
| Dry control | 1.98 | — | 1.8 | 1.23 | 1.0 | 0.49 | 0.13 |
| % of Pretreatment | 100 | — | 91 | 62 | 51 | 25 | 6.6 |
| Dry Treated | 2.2 | 0.1 | 0.11 | 0.08 | 0.08 | 0.05 | 0.02 |
| % of Pretreatment | 100 | 4.5 | 5.0 | 3.6 | 3.6 | 2.3 | 0.9 |
| Irrigated Control | 3.06 | — | 2 | 1.7 | 2.4 | 16 | 0.02 |
| % of Pretreatment | 100 | — | 65 | 56 | 78 | 52 | 0.6 |
| Irrigated Treated | 1.8 | 0.08 | 0.2 | 0.06 | 0.14 | 0.02 | 0.005 |
| % of Pretreatment | 100 | 5.32 | 11 | 3.3 | 7.7 | 1.1 | 0.2 |

Figure 2:
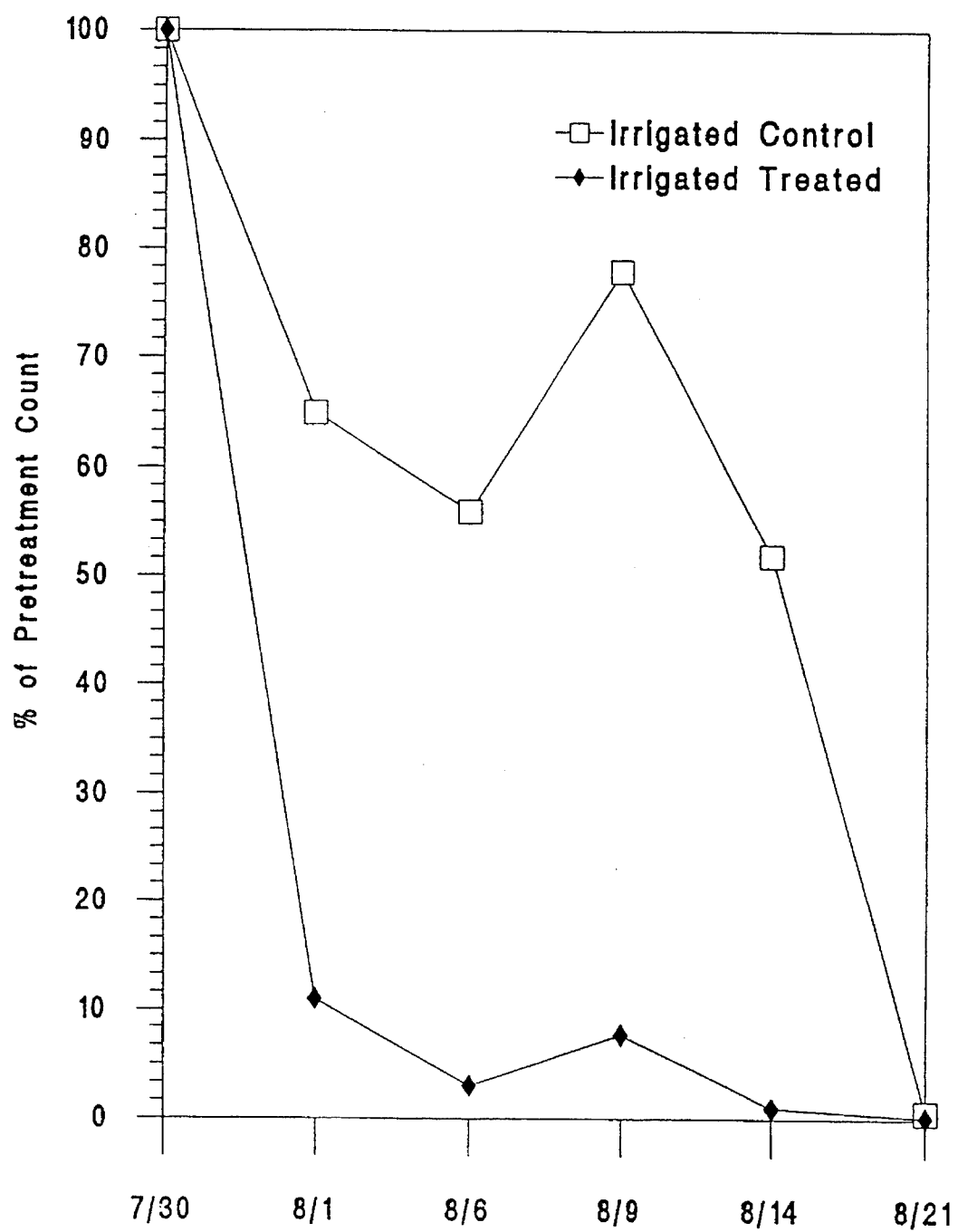
FIG. 2 is a graph showing the control afforded by the present invention over western corn rootworm in irrigated fields.
Figure 3:
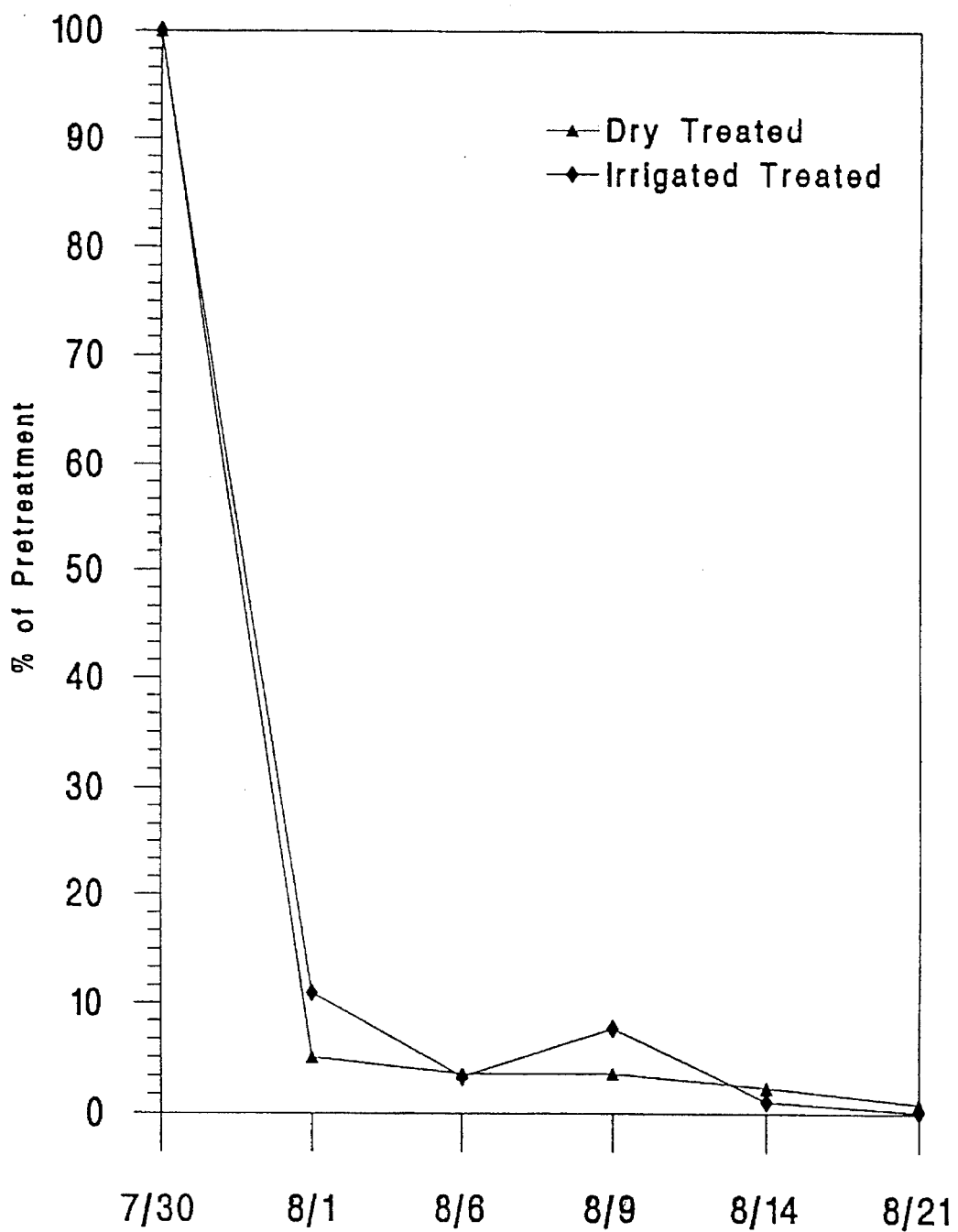
FIG. 3 is a graph showing the control afforded by the present invention over western corn rootworm in dry v. irrigated fields.

The information from Table 6 is graphically presented in FIGS. 1–3. FIG. 1 shows the mean beetle counts of the dry control plants and the plants treated with baits according to the invention without irrigation over a 3 week period. FIG. 2 shows the same type of comparison but in fields that were irrigated by conventional irrigation methods. FIG. 3 compares the dry beetle counts against the irrigated field counts.

As seen from the high levels of control under actual field conditions, bait according to the present invention provides good control over corn rootworm population.

Example 8

In example 8, microspheres from example 1 were aerially applied at a rate corresponding to 0.75 lbs of microspheres (340 g) per acre to two fields (150 acres and 130 acres) exhibiting an infestation of northern corn rootworm. As above, the untreated control field was contiguous and used to monitor area beetle population changes. Table 7 reports the acreage-weighted average beetle count of the test fields and the control field.

TABLE 7

| | Northern Corn Rootworm Tests | | | |
|---|---|---|---|---|
| | 8/9 (Pretreatment) | 8/13 (4 days) | 8/20 (11 days) | 8/27 (18 days) |
| Control | 1.5 | 3.5 | 1.3 | 0.8 |
| % of Pretreatment | 100 | 233 | 87 | 53 |
| Treated Fields | 1.7 | 0.2 | 0.1 | 0.1 |
| % of Pretreatment | 100 | 12 | 6 | 6 |

As an examination of table 7 shows, the area beetle population increased by more than twice in the 4 days after treatment. Notwithstanding this increase, baits according to the present invention continued to provide, good population control through this increased population period and for the succeeding two weeks.

The examples presented herein are intended to serve as an aid to understanding the present invention. Specific materials and particle sizes exemplified are not intended to serve as a limitation on the scope of the appended claims.

We claim:

1. A bait composition useful for controlling diabroticine beetle populations, said composition comprising:
   particulate composite baits exhibiting sizes of less than 1000 μm in diameter and comprising:
   (a) 0.01–99 wt % of diabroticidal insecticide particles;
   (b) 0.01–99 wt % of a feeding stimulant comprising a cucurbitacin-containing material wherein the feeding stimulant is present in amounts effective to stimulate compulsive feeding in diabroticine beetles and said feeding stimulant is homogeneously admixed with said insecticide throughout said bait; and
   (c) a binding agent comprising gelatin and a gum for binding together the insecticide particles and the feeding stimulant.

2. A bait composition as in claim 1 wherein said feeding stimulant comprises natural plant tissue containing cucurbitacin.

3. A bait composition as in claim 2 wherein said natural plant tissue comprises dried root tissue from *Cucurbita foetidissima*.

4. A bait composition as in claim 1 wherein said diabroticidal insecticide comprises a carbamate.

5. A bait composition according to claim 4 wherein said diabroticidal insecticide comprises carbaryl.

6. A bait composition as in claim 1 further comprising a carrier for said bait.

7. A bait composition as in claim 6 wherein said carrier comprises corn cob grit.

8. A bait as in claim 1 wherein said binder comprises carrageenan gum and pork gelatin.

9. A bait as in claim 1 wherein said binding agent further comprises at least one material selected from the group consisting of preservatives, plasticizers, and sticking agents.

10. A bait as in claim 9 wherein said binding agent further comprises a preservative and a sticking agent.

11. A bait as in claim 1 wherein said bait exhibits a spray dried particle size of less than 600 μm in diameter.

12. A bait particle as in claim 8 wherein said diabroticidal insecticide comprises carbaryl, the feeding stimulant particles contain buffalo gourd root powder, and said bait further comprises sorbitol and sodium benzoate.

13. A method for controlling diabroticine beetle populations by a process comprising:
    applying to soil in an area exhibiting a diabroticine beetle larvae infestation an amount of a particulate bait exhibiting a size of less than 1000 μm in diameter that is effective to kill at least a portion of the larvae in said area upon consumption thereof by said larvae wherein said brat contains a homogeneous mixture comprising:
    (a) diabroticidal insecticide particles;
    (b) feeding stimulant containing a cucurbitacin-containing material wherein said feeding stimulant is present in amounts effective to stimulate compulsive feeding in diabroticine beetle larvae and said feeding stimulant is homogeneously admixed with said insecticide throughout said bait; and
    (c) a binding agent comprising gelatin for binding together the insecticide particles and the feeding stimulant.

14. A method according to claim 13 wherein the applying step comprises applying less than about 10 pounds per acre of said bait to soil.

15. A method according to claim 14 wherein the applying step comprises applying less than about 5 pounds per acre of said bait to soil.

16. A method according to claim 15 wherein the applying step comprises applying less than about 1 pound per acre of said bait to soil.

17. A method according to claim 13 wherein the applying step comprises applying about 5 to about 200 grams of active insecticide ingredient per acre to soil.

18. A method for controlling diabroticine beetle populations on plants consumed by diabroticine beetles by a process comprising:
    applying to an area exhibiting a diabroticine beetle infestation an amount of a finely divided particulate bait exhibiting a size of less than 1000 μm in diameter that is effective to kill at least a portion of the beetles in said area upon consumption thereof by said beetles wherein said bait comprises a homogeneous mixture comprising: (a) diabroticidal insecticide particles; (b) a feeding stimulant comprising a cucurbitacin-containing material wherein the feeding stimulant is present in amounts effective to stimulate compulsive feeding in diabroticine beetles; and (c) a binding agent comprising gelatin for binding together the insecticide particles and the feeding stimulant wherein said feeding stimulant are homogeneously admixed with said insecticide particles throughout said bait.

19. A method according to claim 18 wherein the applying step comprises applying less than about 5 pounds per acre of said bait on the upper surfaces of said plants.

20. A method according to claim 19 wherein the applying step comprises applying less than about 1 pound per acre of said bait on the upper surfaces of said plants.

21. A method according to claim 18 wherein the applying step comprises applying about 100 to about 200 grams of active insecticide ingredient per acre on the upper surfaces of said plants.

22. A method as in claim 18 wherein the applying step comprises applying a bait containing a binding agent which comprises carrageenan gum and pork gelatin.

23. A bait composition useful for controlling diabroticine beetle populations, said composition comprising:
    particulate composite baits exhibiting sizes of less than 1000 μm in diameter and comprising:
    (a) 0.01–99 wt % of carbaryl particles;
    (b) feeding stimulant comprising a cucurbitacin wherein said feeding stimulant is homogeneously admixed with said insecticide particles throughout said bait and is present in amounts effective to stimulate compulsive feeding in diabroticine beetles; and
    (c) a binding agent comprising carrageenan gum, pork gelatin, sorbitol, and sodium benzoate for binding together the insecticide particles and the feeding stimulant.

24. A method according to claim 17 wherein the applying step comprises applying about 5 to about 100 grams of active insecticide ingredient per acre to soil.

25. A method according to claim 24 wherein the applying step comprises applying about 20 to about 50 grams of active insecticide ingredient per acre to soil.

26. A method for controlling diabroticine beetle populations by a process comprising:
    applying to soil in an area exhibiting a diabroticine beetle larvae infestation an amount of a finely divided particulate bait exhibiting a size of less than 1000 μm in diameter that is effective to kill at least a portion of the larvae in said area upon consumption thereof by said larvae wherein said bait contains a homogeneous mixture which comprises:

(a) 0.01–99 wt % diabroticidal insecticide particles;

(b) feeding stimulant containing a cucurbitacin-containing material wherein the feeding stimulant is present in amounts effective to stimulate compulsive feeding in diabroticine larvae and is homogeneously admixed with said insecticide particles throughout said bait; and (c) a binding agent comprising carrageenan gum, pork gelatin, sorbitol, and sodium benzoate for binding together the insecticide particles and the feeding stimulant.

27. A method as in claim 18 wherein the applying step comprises:

applying said particulate bait wherein the binding agent therein further comprises at least one material selected from the group consisting of preservatives, plasticizers, and sticking agents.

28. A method as in claim 27 wherein the applying step comprises:

applying said particulate bait wherein the binding agent therein further comprises a preservative and a sticking agent.

29. A method as in claim 18 wherein the applying step comprises:

applying said particulate bait which exhibits a spray dried particle size of less than 600 µm in diameter.

30. A method as in claim 29 wherein the applying step comprises:

applying said particulate bait wherein said diabroticidal insecticide particles contain carbaryl, the feeding stimulant comprises particles containing buffalo gourd root powder, and said binder further comprises sorbitol and sodium benzoate.

31. A method for controlling diabroticine beetle populations on plants consumed by diabroticine beetles by a process comprising:

applying to an area exhibiting a diabroticine beetle infestation an amount of a finely divided particulate bait exhibiting a size of less than 1000 µm in diameter that is effective to kill at least a portion of the beetles in said area upon consumption thereof by said beetles wherein said bait comprises a homogeneous mixture comprising:

(a) 0.01–99 wt % carbaryl particles;

(b) a feeding stimulant comprising a cucurbitacin-containing material wherein the feeding stimulant is present in amounts effective to stimulate compulsive feeding in diabroticine beetles and is homogeneously admixed with said insecticide particles throughout said bait; and (c) a binding agent comprising carrageenan gum, pork gelatin, sorbitol, and sodium benzoate for binding together the insecticide particles and the feeding stimulant.

* * * * *